US006207170B1

(12) United States Patent
Popescu et al.

(10) Patent No.: US 6,207,170 B1
(45) Date of Patent: Mar. 27, 2001

(54) PATIENT-SPECIFIC WHITE BLOOD CELL MALIGNANCY VACCINE FROM MEMBRANE-PROTEOLIPOSOMES

(75) Inventors: Mircea C. Popescu, Plansboro; Lawrence Boni, Monmouth Junction; Richard J. Robb, Princeton Junction; Michael M. Batenjany, Hamilton, all of NJ (US)

(73) Assignee: Biomira U.S.A., Inc., Cranbury, NJ (US)

( * ) Notice: Subject to any disclaimer, the term of this patent is extended or adjusted under 35 U.S.C. 154(b) by 0 days.

(21) Appl. No.: 09/231,650

(22) Filed: Jan. 15, 1999

Related U.S. Application Data
(60) Provisional application No. 60/071,702, filed on Jan. 16, 1998.

(51) Int. Cl.[7] .................. A61K 39/00; A61K 39/385; A61K 39/39; A61K 47/00; A61K 47/02
(52) U.S. Cl. ................... 424/277.1; 424/184.1
(58) Field of Search .................. 424/1.11, 1.21, 424/1.29, 1.41, 1.57, 1.69, 1.73, 184.1, 277.1

(56) References Cited

U.S. PATENT DOCUMENTS

| 4,816,249 | 3/1989 | Levy et al. . |
| 5,030,621 | 7/1991 | Bystryn . |
| 5,194,384 | 3/1993 | Bystryn . |
| 5,635,188 | 6/1997 | Bystryn .......................... 424/277.1 |

FOREIGN PATENT DOCUMENTS

| 0 283 443 | 9/1988 | (EP) . |
| WO 94/08601 | 4/1994 | (EP) . |
| 97/29769 | 8/1997 | (WO) . |

OTHER PUBLICATIONS

Zintl et al.; "Prerequisites and Possibilities of Immunotherapy In Acute Leukemia"; Apr. 15, 1976; pp. 227–231; XP002103820.

Neil Gershman, Dean Johnston and Jean–Claude Bystryn; Potentiation of Melanoma Vaccine Immunogenicity by Interleukin 2 Liposomes; Vaccine Research, vol. 3, No. 2, 1994; pp. 83–92.

J.J. Bergers, W. Den Otter and D.J.A. Crommelin; Vesicles for tumour–associated antigen presentation to induce protective immunity: preparation, characterization and enhancement of the immune response by immunomodulators; *Journal of Controlled Release*, 29 (1994) pp. 317–327.

Joep J. Bergers, Willem Den Otter and Daan J.A. Crommelin; Liposome–Based Cancer Vaccines; Journal of Liposome Research, 6(2), pp. 339–355 (1996).

Abul K. Abbas, Andrew H. Lichtman, M.D., Jordan S. Pober, M.D.; Cellular and Molecular Immunology; Saunders Text and Review Series; pp. 372–373, 1994.

Stephen J. LeGrue, Barry D. Kahan and Neal R. Pellis; Extraction of a Murine Tumor–Specific Transplantation Antigen With 1–Butanol. I. Partial Purification by Isoelectric Focusing; Jnci. vol. 65, No. 1, Jul. 1980; pp. 191–196.

Larry W. Kwak, Michael J. Campbel, Andrew D. Zelenetz, and Ronald Levy; Combined Syngeneic Bone Marrow Transplantation and Immunotherapy of a Murine B–Cell Lymphoma; Active Immunization With Tumor–Derived Idiotypic Immunoglobulin; Blood; vol. 76, No. 11 (Dec. 1, 1990); pp. 2411–2417.

Larry W. Kwak, M.D., Michael J. Campbell, Ph.D., Debra K. Czerwinski, B.S., Sarah Hart, B.S., Richard A. Miller, M.D., and Ronald Levy, M.D.; Induction of Immune Responses in Patients with B–Cell Lymphoma Against the Surface–Immunoglobulin Idiotype Expressed by Their Tumors; Induction of Immune Responses in B–Cell Lymphoma, vol. 327, No. 17; pp. 1209–1215, 1992.

Tamauchi et al. Enhancement of immunogenicity by incorporation of lipid A into liposomal model membranes and its application to membrane–associated antigens. Immunology 50:605–612, 1983.*

* cited by examiner

*Primary Examiner*—Sheela Huff
*Assistant Examiner*—Alana M. Harris
(74) *Attorney, Agent, or Firm*—Foley & Lardner

(57) ABSTRACT

Membrane-proteoliposome structures (MPs) are useful in preparing patient-specific vaccines against specific white blood cell (WBC) malignancies. The inventive MPs typically contain a membrane component derived from a specific WBC. Other useful components include immunostimulators and exogenous lipids. The resulting vaccines are both patient- and malignancy-specific.

21 Claims, 2 Drawing Sheets

PATIENT-SPECIFIC WHITE BLOOD CELL MALIGNANCY VACCINE FROM MEMBRANE-PROTEOLIPOSOMES

This application claims priority to provisional U.S. Application Ser. No. 60/071,702, filed Jan. 16, 1998.

BACKGROUND OF THE INVENTION

The present invention is directed to the production of novel compositions, useful as vaccines for treating white blood cell (WBC) malignancies. The invention relates to a liposomal, patient-specific vaccine comprised of WBC membranes that may be formulated by adding other lipids and/or immunostimulators, thereby forming a novel membrane-proteoliposome (MP) structure.

Known vaccines typically utilize either purified antigen or attenuated pathogen as the immunogen. However, attenuated vaccines can actually cause the infection against which a person is being immunized. On the other hand, purified antigens may not induce a longterm immune response and sometimes induce no response at all. In contrast to the short-term immune response obtained by direct immunization with certain antigens, presentation of the antigen in the presence of liposomes can induce a long-term response which is essential for any effective vaccine.

Although typically formed from purified or partially purified lipids, liposomes may also be formed, at least in part, from cell membranes of malignant cells which contain potential antigens. Due to the presence of membrane associated antigens, these membrane derived preparations may be used as malignancy-specific vaccines. Indeed, some types of membrane-derived preparations have been used as tumor specific antigens (TSA) to treat melanomas and murine SL2 lymphosarcoma. See Gershman et al., Vaccine Res. 3:83–92 (1994); Bergers et al., J. Confr. Rel. 29:317–27 (1994); Bergers et al., J. Liposome Res. 6:339–35 (1996). In these cases, the production of vaccine suffered from serious disadvantages. Namely, they required pooling culture adapted cells to achieve large amounts of the desired cell populations, use of whole γ-irradiated tumor cells, detergent solubilization or butanol for crude extraction of tumor-associated antigens (TAA). See Gershman et al. (1994), supra; Abbas, et al., CELLULAR AND MOLECULAR IMMUNOLOGY, pp.372–73 (W. B. Saunders Company, Philadelphia 1994); Bergers et al. (1994), supra; LeGrue et al., J. Natl. Cancer Inst. 65:191–96 (1980). This approach, moreover, is not patient-specific.

The art is also aware of some vaccines directed to certain B cell malignancies. Typically, however, attempts at producing vaccines for B-cell lymphoma have relied on the costly and time consuming hybridoma technology. These methods depend on generating a hybridoma able to produce the tumor-specific immunoglobulin (Ig) in enough quantity to be then used as a vaccine. Kwak et al., Blood 76:2411–17 (1990); Kwak et al., N. Engl. J. Med. 327:1209–15 (1992). Known B-cell lymphoma vaccines employ Ig idiotype (Id) to generate anti-idiotype antibodies to B-cells. Levy et al., PCT/US94/08601 (Feb. 23, 1995); Levy et al., U.S. Pat. No. 4,816,249 (1989). Similarly, known melanoma vaccines involved harvesting cell surface antigens which are shed during culturing. Bystryn, U.S. Pat. No. 5,635,188 (1997); Bystryn, U.S. Pat. No. 5,194,384 (1993); Bystryn, U.S. Pat. No. 5,030,621 (1991).

There is, therefore, an unmet need in the art for improved liposome-based vaccines. A particular need exists for improved vaccines against white blood cell malignancies.

SUMMARY OF THE INVENTION

Accordingly, it is an object of the invention to provide novel vaccine compositions that overcome the above-identified and other deficiencies in the art. According to this object of the invention, membrane-proteoliposomes (MPs) are provided which are malignancy-specific, patient-specific and are easily prepared. Thus, in one embodiment, MPs are provided which comprise the cell membrane of a white blood cell malignancy, at least one immunostimulator and at least one lipid, where the lipid may be added in the form of lipid powder, or preformed liposomes. Another embodiment of the invention provides novel vaccine formulations which comprise an MP comprising the cell membrane of a white blood cell and may include at least one immunostimulator.

It is yet another object of the invention to provide methods for preparing MPs and vaccines which also overcome the deficiencies in the art. According to this object of the invention, methods are disclosed that do not rely on harvesting the vaccine antigen, hybridoma production or other intermediate steps. The inventive methods comprise formulating a vaccine directly from isolated antigen-containing membranes from patients' own white blood cells (WBCs), thus rendering them highly effective and patient-specific.

DETAILED DESCRIPTION

Introduction

Figure 1:
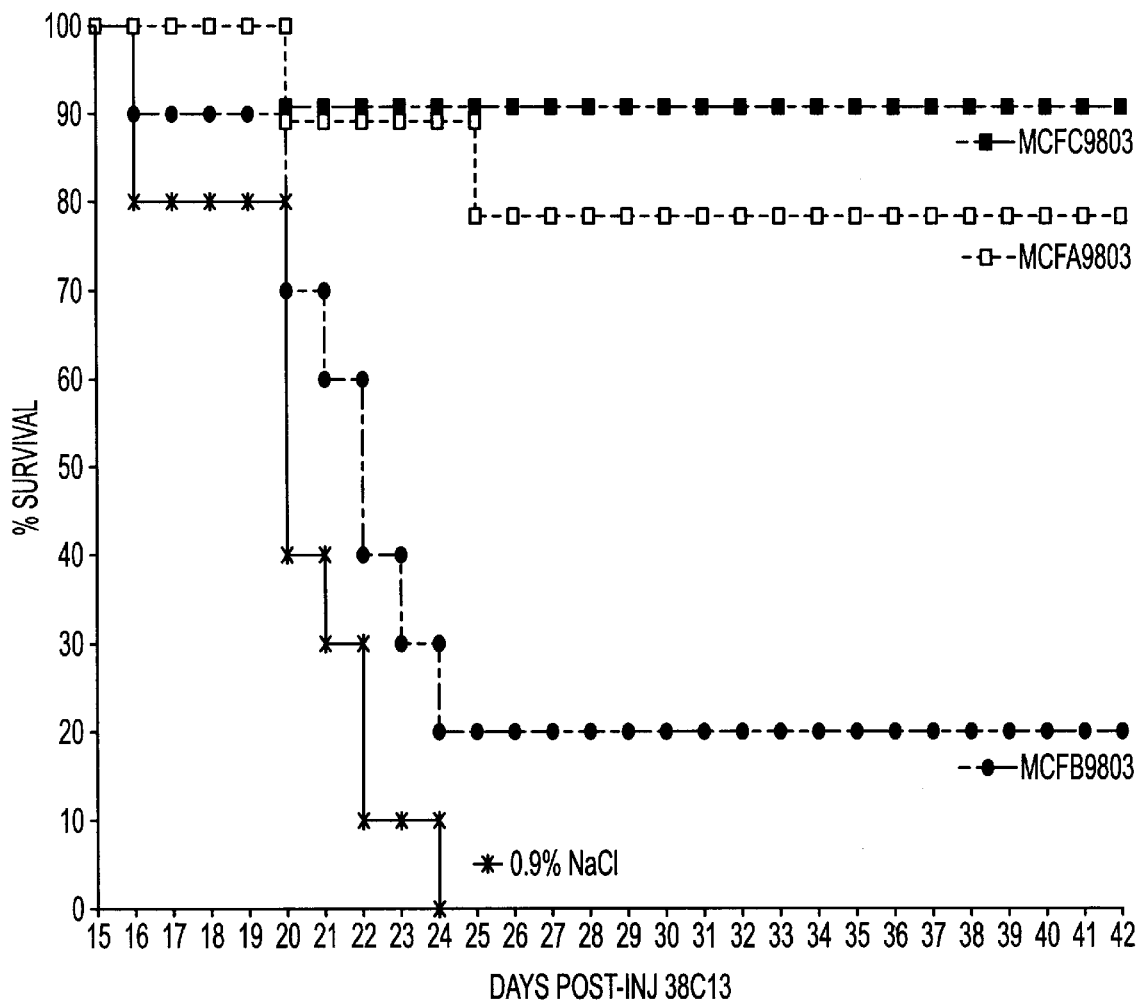
FIG. 1 exhibits the survival results after mice were vaccinated with the MP formulation described in Example 5.

The instant invention provides membrane-proteoliposome structures (MPs) that are useful in formulating patient-specific vaccines for treating white blood cell (WBC) malignancies.

The inventors previously described a proteoliposomal vaccine made of antigen idiotype (Id) and interleukin-2 (IL-2) proteins within a liposomal structure (Popescu, et al., PCT/US97/02351). In contrast to that earlier work, a novel liposomal structure is disclosed herein, called a membrane-proteoliposome (MP), which usually comprises phospholipid, integral membrane from a malignant WBC and a potent immunostimulator. The present invention is based in part on the discovery that membranes from WBC malignancies can be fused with other components to form an effective vaccine against the malignancy.

All WBCs, including polymorphonuclear cells (PMN), monocytes and T- or B-lymphocytes, are subject to malignant transformation leading to a spectrum of diseases. For example, B-cell malignancy includes non-Hodgkin's lymphomas, chronic lymphocytic leukemia and multiple myeloma. The present invention has relevance in treating or preventing many such malignancies.

In preparing the inventive vaccines, WBC's can be obtained directly from the patient to isolate the intact membranes, rich in tumor-specific antigens (TSA) and tumor-associated antigens (TAA). In general cells will be enucleated and their plasma membranes separated from other components (e.g., mitochondria, lysosomes). The plasma membranes typically are washed to remove cellular contaminates, which may include cytoskeletal structures, and the separation material. The plasma membrane suspensions may then be exposed to mechanical size reduction, for example, by extrusion, homogenization or other shearing methods. This will allow for filtration through a sterilizing filter. The WBC membranes may also be detergent solubilized, reconstituted with lipids of choice then size reduced. In lieu of mechanical size reduction methods, the isolated membranes may be sterilized by, for example, γ-irradiation.

The isolated malignant cell membranes, alone or in combination with added lipids, can then be used to entrap an immunomodulator. The extent of entrapment of immunomodulator, immunogenicity and efficacy of the MP as a vaccine can be modulated by the nature of the constitutive lipids. A thus optimized MP formulation may then be used to vaccinate the patient against his/her specific WBC malignancy.

The present invention is particularly useful in vaccinating against non-Hodgkin's lymphomas. These lymphomas are characterized by the expression of monotypic immunoglobulin (Ig) which can serve as a tumor-specific antigen. In addition, these cells typically express surface molecules involved in antigen presentation, such as class I and class II MHC molecules (with associated TSA or TAA peptide), and costimulation, such as adhesion proteins and B7.1 and B7.2 (CD80 and CD86). In particular, the presence of a class I MHC molecule in the inventive formulation will potentially enhance the cytotoxic immune response against the tumor. These characteristics make the B-cell lymphoma plasma membrane an attractive candidate that can be used as a potentially strong immunogenic tool in active specific immunotherapy.

The present invention provides a proteoliposomal, patient-specific vaccine for WBC malignancies that, in one embodiment, is produced by entrapping a potent immunomodulator together with malignant white blood cell membranes. The resulting membrane-proteoliposome can be either (1) a cell-derived membrane patched with at least one added membrane-forming lipid or (2) a lipid membrane (e.g., a liposome) patched with cell-derived membrane. By "patched" is meant that the resulting MP is non-homogeneous with respect to the component lipid sources. Thus, contiguous portions of the MP will be essentially WBC membrane-derived, while others will be derived essentially from the added membrane-forming lipids. In three examples below, MP formulations are described which contain membrane from a mouse B-cell lymphoma (38C13), and which were used as effective vaccines in a mouse model of non-Hodgkin's B-cell lymphoma.

Vaccine Compositions of the Invention

The vaccine compositions of the invention typically comprise at least one membrane component of a malignant white blood cell. Important membrane components specifically include components involved in immunity. Components involved in immunity can include any macromolecules, such as proteins, lipids and carbohydrates, which are normally an integral part of, or simply associated with, the cell membrane. Other organic and inorganic substances which are similarly associated with the cell membrane also are included. Some preferred components involved in immunity include tumor-specific antigens (TSA), tunor associated antigens (TAA), major histocompatability (MHC) antigens (class I and class II molecules) and costimulatory molecules.

Costimulatory molecules are second signal immunostimulators associated with T cell activation. Costimulatory molecules typically are cell surface molecules which act in conjunction with primary immune signals, i.e., antigen presented by MHC molecules, to generate an immune response. Thus, acting in concert, primary and secondary signal molecules facilitate antigen presentation by antigen presenting cells (APC) to T cells. Examples of costimulatory molecules include cellular adhesion molecules and CD-40. Specific preferred costimulatory molecules include B7.1, B7.2 and ICAM-1 (CD 56).

Preferably, the membrane component takes the form of an isolated plasma membrane (in whole or in part). The isolated plasma membrane preferably is constituted of lipid which is membrane-forming. Thus, all components normally integral to or associated, with the cell plasma membrane, including components involved in immunity, typically are present. This preferred membrane component will usually be isolated from a patient sought to be vaccinated. Thus, the resultant vaccine comprising this membrane component will be patient-specific and specific for the WBC malignancy from which the membrane component is isolated. It is envisioned that a vaccine formulated with a membrane component from one patient will be useful in vaccinating another patient, given similar antigenic determinants. Of course, it is also possible, due to cross-reactivity or common antigenic determinants, that the vaccine for one malignancy will prove useful in vaccinating against another malignancy. Thus, as used herein, "patient-specific" refers to the fact that the vaccine is derived from a particular patient (it thus will be useful in treating that same patient), not that it is useful only to treat the patient or the specific malignancy from which it is derived. Although the patient will normally be human, non-human animals may also be patients.

The inventive vaccine compositions can be made specific for any white blood cell malignancy. The clinician will be familiar with the various types of white blood cells and their malignancies. Representative white blood cells include polymorphonuclear cells (PMNs), monocytes, T-lymphocytes and B-lymphocytes. Some representative white blood cell malignancies include lymphomas, leukemias, and myelomas. Other white blood cell malignancies are known in the art. Further examples of WBC malignancies are found in McCance et al., PATHOPHYSIOLOGY: THE BIOLOGIC BASIS OF DISEASE IN ADULTS AND CHILDREN, chapters 24 and 25, pp. 800–855 (The C.V. Mosby Company 1990), which are hereby incorporated by reference.

Some preferred vaccine compositions further comprise at least one immunostimulator. Immunostimulators specifically include any substance that can be used to modulate the immune response. Especially useful immunostimulators are those which can be used to stimulate the specific immune response to components involved in immunity. Exemplary classes of such useful immunostimulators include: lymphokines, such as IL-2, IL-4 and IL-6; interferons, such as IFN-γ and IFN-α; other cytokines, such as GM-CSF and M-CSF; and adjuvants, such as Lipid A, monophosphoryl lipid A (MPL), or muramyl dipeptide (MDP). Immunostimulators may be used alone or in any combination with one another. Some compositions comprise at least two immunostimulators, such as IL-2 and MPL or MDP, and other combinations of cytokines with adjuvants.

Other preferred vaccine compositions comprise lipids other than those present in the cell membrane component (i.e., from an exogenous source). These "exogenous" lipids may be from natural or synthetic sources. Preferred lipids include phospholipids, glycolipids, and especially saturated phospholipids. Saturated phospholipids include 1,2-dimyristoylphosphatidylcholine (DMPC), 1,2-dipalmitoylphosphatidylcholine (DPPC), 1,2-dimyristoylphosphatidylglycerol (DMPG). Other useful lipids include cholesterol and derivatives thereof. Of course combinations of these and other lipids are also useful.

Methods for Preparing the Inventive Vaccines

Preparing an inventive vaccine involves first isolating WBC membrane components, free of other cellular components. One such example is provided below as Example 4. According to a preferred embodiment, isolated membranes typically are combined with other lipids and/or immunostimulators to form MPs. There are many liposome-forming methods known in the art and any of these standard methods may be employed in preparing the present MP.

In one exemplary method MPs can be prepared containing IL-2 as an immunostimulator. The IL-2 is mixed with the WBC membranes and entrapped by freeze/thawing from −70° C. to 37° C., followed by brief vortexing and short bath sonication (30 seconds). The preparation can include the addition of a suitable lipid powder at 50 to 300 mg/nL (final). Thus, using this method MPs can be formed independent of exogenous lipids or from WBC membrane components mixed with exogenous lipids.

MPs can also be prepared containing only WBC membrane components, which may be fused with preexisting liposomes which comprise exogenous lipids. A WBC membrane suspension is lyophilized then hydrated with a suitable liquid, for example, water, normal saline solution (NSS) or a suitable buffer. The hydration liquid may contain an inununomodulator. Thus, MPs comprising WBC membrane components are formed. In addition, pre-formed multilamellar vesicles (MLVs), composed of suitable exogenous liposome-competent lipids, may be mixed with the WBC membrane suspension prior to lyophilization. The MLVs may contain a pre-incorporated immunomodulator, in which case the lyophilized preparation is hydrated with a suitable liquid, which may contain at least one immunomodulator. Thus, in any method for preparing MPs, any combination of multiple immunostimulators may be incorporated at any suitable point in the process.

In another method, the WBC membrane suspension is size reduced by extrusion, homogenization or other shearing methods to form small unilamellar vesicles (SUVs). The SUVs are then lyophilized and hydrated with a suitable liquid, optionally containing an immunomodulator. SUVs prepared from exogenous lipids also may be added prior to the lyophilization step. In addition, the immunomodulator may be mixed with the SUV's prior to lyophilization. In any event, whenever the lyophilized preparation is hydrated, the liquid may contain an immunomodulator.

In yet another method, a WBC membrane suspension is added to MLVs comprising exogenous lipids. The resulting mixture is lyophilized and hydrated with water, NSS or buffer followed by size reduction (extrusion, homogenization or other shearing methods) to form SUV's. An immunomodulator may be added and the mixture is allowed to fuse overnight.

Another method involves adding a WBC membrane suspension to MLVs comprising exogenous lipids. The mixture is lyophilized and hydrated with a suitable liquid. The resulting suspension is size reduced by extrusion, homogenization or other shearing methods to form SUVs. The SUVs are lyophilized and hydrated with a suitable liquid, optionally containing an immunomodulator.

Also, the WBC membrane suspension may be size reduced by extrusion, homogenization or other shearing methods to form SUVs. An immunomodulator is added to the SUVs and the mixture is then allowed to fuse overnight.

Vaccines may also be formulated with a pharmaceutically acceptable excipient. Such excipients are well known in the art, but typically should be physiologically tolerable and inert or enhancing with respect to the vaccine properties of the inventive compositions. When using an excipient, it may be added at any point in formulating the vaccine or it may be admixed with the completed vaccine composition.

Vaccines may be formulated for multiple routes of administration. Specifically preferred routes include intramuscular, percutaneous, subcutaneous, or intradermal injection, aerosol, oral or by a combination of these routes, at one time, or in a plurality of unit dosages. Administration of vaccines is well known and ultimately will depend upon the particular formulation and the judgement of the attending physician.

Vaccine formulations can be maintained as a suspension, or they may be lyophilized and hydrated later to generate a useable vaccine.

EXAMPLES

Example 1

Isolation of plasma cell membranes

This example demonstrates a method for isolating WBC plasma membranes. Frozen (−70° C.) 38C13 murine B-lymphoma cells were quick-thawed at 37° C., suspended at $2 \times 10^8$ cells/mL in homogenization buffer (HB). The composition of HB was 0.25 M sucrose, 10 mM Tris/HCl, 1 mM $MgCl_2$, 1 mM KCl, phenylmethylsulfonyl fluoride (PMSF, 2 mM, final), trypsin-chymotrypsin inhibitor (200 µg/mL, final), DNase (10 µg/mL, final) and RNase (10 µg/mL, final), pH 7.3. The 38C13 cells were enucleated in a hand-held Dounce homogenizer (20–30 passes while on ice). The slurry was spun at 500×g (10 minutes, 4° C.) and the supernatant collected. The pellet was resuspended in HB and the homogenization and centrifugation steps repeated until the pellet, as judged by light microscopy, was essentially free of intact cells (~95% nuclei only). The pooled supernatants were layered on a discontinuous sucrose gradient (p=1.11, 1.18 and 1.25 g/mL) and spun at 28K×g (30 minutes, 4° C.). The plasma membrane-rich region was collected (p=1.11/1.18 interface), diluted two-fold with NSS and spun 28K×g (1 hour, 4° C.). The pellet was again diluted two-fold with the NSS and respun as above. The washed membranes were resuspended in a minimal amount of NSS and stored at 4° C.

Example 2

Preparation of Membrane Proteoliposomes

This example demonstrates a method of formulating a vaccine from isolated WBC membranes. Experimental vaccine MB-RM-1A was formulated as follows: DMPC powder (1 g), 4 mL of the isolated 38C13 membranes (225 µg/mL IgM) in NSS and 160 ul of IL-2 ($1.25 \times 10^8$ IU/mL) were placed in a 5 mL sterile glass vial, immediately vortexed, heated to 37° C. for 15 minutes in a water bath, then sonicated at 37° C. for 30 seconds in a bath sonicator. This suspension was subjected to three freeze/thaw cycles as follows:

1) Freezing at −70° C. (dry ice/methanol bath) for 15 minutes

2) Thawing at 37° C. (water bath) for 15 minutes

3) Vortexing briefly

4) Sonicating for 30 seconds in a bath sonicator at 37° C.

The preparation was adjusted to a total volume of 5 mL with NSS and stored at −70° C.

Example 3

Comparative Vaccine Effectiveness

This example demonstrates the effectiveness of exemplary vaccines produced according to the invention, and particularly the freeze/thaw method of Example 2. The results presented below, and depicted in FIG. 1, show that the vaccinated mice survived a lethal B-cell lymphoma challenge.

As seen in the following Table, the exemplary freeze-thaw MP vaccine, MB-RM-1A, effectively protected 85% of the mice challenged with a lethal dose of 38C13 lymphoma cells. By comparison, as summarized below, the survival associated with control vaccine formulations was lower.

TABLE

| Vaccine | Description | Percent Survival |
| --- | --- | --- |
| MB-RM-1A | MP vaccine | 85 |
| 4C5-Id | Non-specific antigen | 0 |
| 38C13-Id | Control vaccine | 10 |
| 38C13-Id-KLH | Control vaccine | 40 |
| OV XIV-2 | Liposomal vaccine | 50 |

The foregoing sample designations correspond to the following: 4C5-Id is a non-specific antigen control; 38C13-Id is a vaccine consisting of soluble 38C13 immunoglobulin; 38C13-Id-KLH is a vaccine consisting of a conjugate between keyhole limpet hemocyanin and soluble 38C13; OV XIV-2 is a liposomal vaccine containing soluble 38C13-Id and IL-2. See Kwak et al. J. Immunol. 160: 3637–3641 (1998); Popescu et al. PCT/US97/02351.

Example 4
Comparative Vaccine Effectiveness

Preparation. A frozen (−70° C.) pellet of 38C13 cells was quickly thawed at 37° C. in a water bath, then placed on ice. All subsequent treatments, unless otherwise specified were carried out on ice at 4° C. The pellet was washed with (5) volumes of ice cold PBS at 1K×g×10 minutes. The pellet was resuspended in ice-cold NSS containing 2 mM phenylmethylsulfonyl fluoride (PMSF), and 100 µg/mL each of DNAse and RNAse. The cells were enucleated by emulsification through a 22 gauge needle (50 passes) and by using a hand held Dounce homogenizer (50 passes). The suspension was spun to pellet the nuclei at 330×g×10 minutes and the supernatant was layered on a Nycodenz gradient (ρ=1.22) and spun at 60K×g×1 hour. WBC plasma membranes were collected at the water/Nycodenz interface and washed with (7) volumes of NSS at 60K×g×30 minutes. The pelleted membranes were resuspended in NSS. A portion of these membranes was used to formulate MCFC9803 using the freeze/thaw method as described in Example 2. The rest of the washed cell membranes were homogenized at ~22K psi (15–20 passes) and used to formulate preparations MCFA9803 and MCFB9803. The following describes the experimental design of formulations MCFA9803, MCFB9803 and MCPC9803:

MCFA9803:
a) Homogenized WBC membranes were added to DMPC SUVs and IL-2.
b) The mixture was allowed to coalesce into MLVs by overnight incubation at 19° C. (Boni et al., PCT Application based on U.S. Serial No. 60/060,606 "Multilamellar Coalescence Vesicles (MLCV) Containing Biologically Active Compounds").

MCFB9803:
a) Homogenized WBC membranes were added to DMPC SUVs and lyophilized.
b) MLVs were formed upon reconstitution with buffer containing IL-2.

MCFC9803:
a) DMPC (powder) and IL-2 were added to a suspension of WBC cell membranes.

b) MLVs were formed by the freeze-thaw method detailed in Example 2.

Survival data. FIG. 1 shows the effectiveness of MP vaccines produced according to the invention, and particularly shows survival data after formulation using three different methods for preparation. The results show that the vaccinated mice survived a lethal B-cell lymphoma challenge. The exemplary MP vaccines, MCFA9803 and MCFC9803, effectively protected 78% (7/9) and 90% (9/10), respectively, of the mice challenged with a lethal dose of 38C13 lymphoma cells. Addition of IL-2 after lyophilization and during reconstitution was less effective (MCFB9803, 20% survival). However, all the formulations offer some protection in this model of lymphoma.

Example 5
Membrane Proteoliposome Characterization

Figure 2:
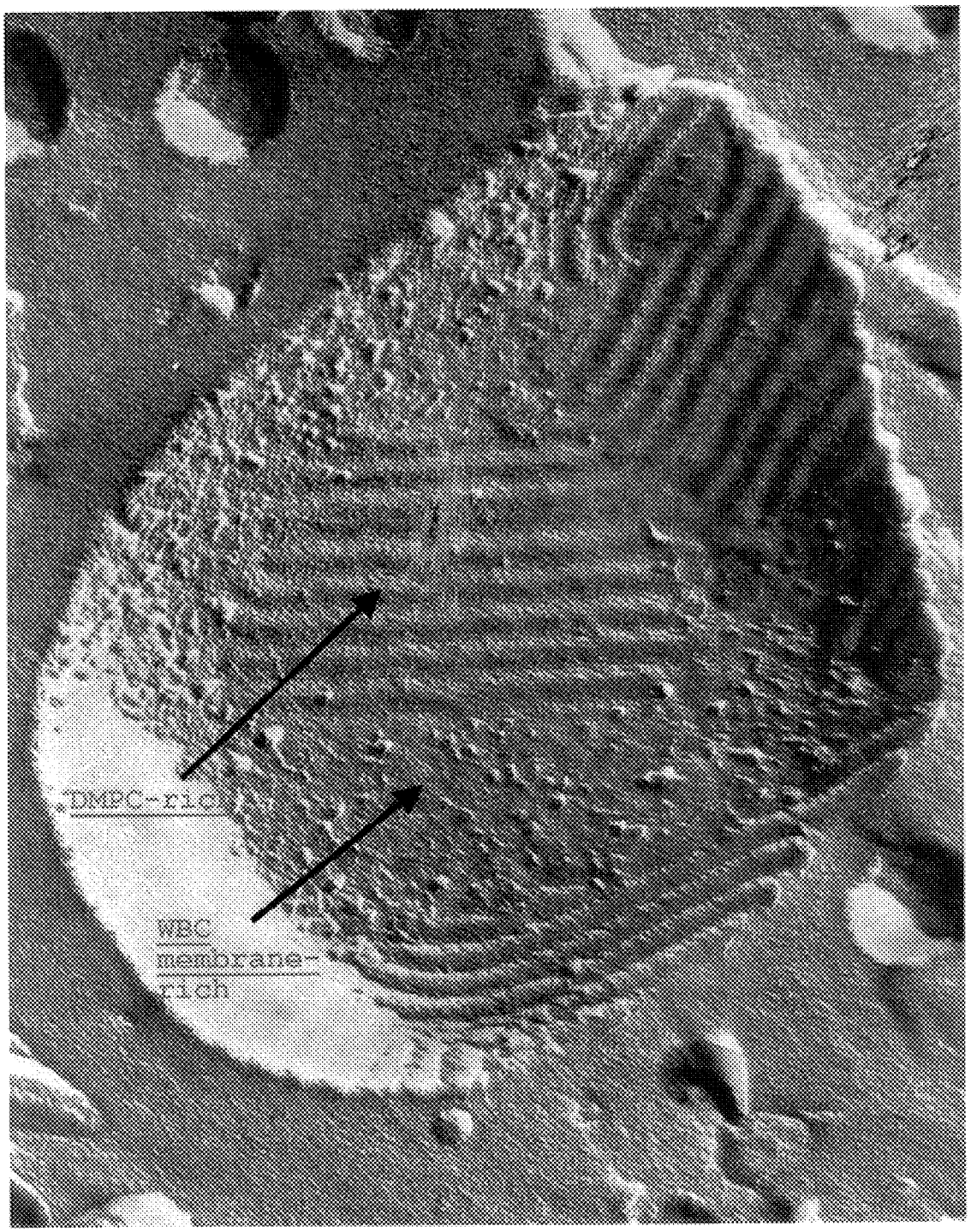
FIG. 2 demonstrates the patching seen in membrane-proteoliposomes, where the patches consist of DMPC-rich and WBC membrane-rich domains (see arrows).

This example demonstrates one alternate method of formulating a vaccine from isolated WBC membranes. SUVs (0.5 mL at 200 mg/mL) prepared from DMPC, WBC membranes (0.5 mL) and IL-2 (19 µl at $1.07 \times 10^8$ IU/mL) are combined and the mixture is lyophilized. Upon reconstitution with 0.5 mL distilled water 59% of the IL-2 is recovered of which 100% is incorporated in the membrane-proteoliposomes and 84% of the IgM is recovered of which 80% is incorporated in the membrane-proteoliposomes. The mean membrane-proteoliposome size is 2.8 microns. Freeze-fracture electron microscopy shown in FIG. 2 reveals membrane-proteoliposomes with the characteristic ripple phase DMPC liposomes mixed with WBC membranes containing intramembranous particles. The two distinct domains in one membrane-proteoliposome define the "patching" of WBC membranes with DMPC lipids.

The foregoing discussion and examples are presented merely for illustrative purposes and are not meant to be limiting. Thus, one skilled in the art will readily recognize additional embodiments within the scope of the invention that are not specifically exemplified.

What is claimed is:

1. A patient-specific vaccine for treating white blood cell malignancy, comprising a membrane-proteoliposome (MP) containing plasma membrane from a malignant white blood cell.

2. A vaccine according to claim 1, wherein said malignant white blood cell is a lymphoma cell.

3. A vaccine according to claim 1, wherein said malignant white blood cell is a leukemia cell.

4. A vaccine according to claim 1, wherein said malignant white blood cell is a myeloma cell.

5. A membrane-proteoliposome (MP), comprising integral membrane from a malignant white blood cell, at least one immunostimulator and an exogenous lipid.

6. An MP according to claim 5, wherein said membrane contains at least one membrane component involved in immunity.

7. An MP according to claim 5, comprising at least two immunostimulators.

8. An MP according to claim 6, wherein said component is selected from the group consisting of a tumor-specific antigen, a major histocompatability complex antigen and a costinulatory molecule.

9. An MP according to claim 8, wherein said costimulatory molecule is CD80 or CD86 or ICAM-1.

10. An MP according to claim 5, wherein said immunostimulator is a lymphokine.

11. An MP according to claim 10, wherein said lymphokine is IL-2.

12. An MP according to claim 5, wherein said immunostimulator is an interferon.

13. An MP according to claim 12, wherein said interferon is IFN-γ.

14. An MP according to claim 5, wherein said immunostimulator is a cytokine.

15. An MP according to claim 14, wherein said cytokine is GM-CSF or M-CSF.

16. An MP according to claim 5, wherein said immunostimulator is an adjuvant.

17. An MP according to claim 16, wherein said adjuvant is selected from the group consisting of monophosphoryl lipid A, lipid A and muramyl dipeptide (MDP) lipid conjugate.

18. An MP according to claim 5, wherein said lipid is a saturated or unsaturated phospholipid or a glycolipid.

19. A MP according to claim 18, wherein said lipid is selected from the group consisting of 1,2-dimyristoylphosphatidylcholine, 1,2-dipalmitoylphosphatidylcholine, 1,2-dimyristoylphosphatidylglycerol, cholesterol and combinations thereof.

20. An MP according to claim 5, wherein said lipid forms a membrane within which said integral membrane is patched.

21. An MP according to claim 5, wherein said lipid forms patches within said integral membrane.

* * * * *